(12) United States Patent
Bistritzky et al.

(10) Patent No.: US 7,481,571 B2
(45) Date of Patent: Jan. 27, 2009

(54) FLAMELESS CANDLE INCORPORATING INSECT REPELLANT DIFFUSER AND AN AMBIENT LIGHT SENSOR

(75) Inventors: Mendel Bistritzky, Hewlett Neck, NY (US); Yosel Avtzon, Brooklyn, NY (US)

(73) Assignees: B&F Product Development, Cedarhurst, NY (US); Fasst Products, LLC, Brooklyn, NY (US)

( * ) Notice: Subject to any disclaimer, the term of this patent is extended or adjusted under 35 U.S.C. 154(b) by 0 days.

(21) Appl. No.: 11/756,785

(22) Filed: Jun. 1, 2007

(65) Prior Publication Data

US 2008/0031784 A1    Feb. 7, 2008

Related U.S. Application Data

(60) Provisional application No. 60/834,597, filed on Aug. 1, 2006.

(51) Int. Cl.
*F21V 33/00* (2006.01)

(52) U.S. Cl. ............... 362/643; 362/253; 362/96; 396/393; 396/390

(58) Field of Classification Search .......... 362/253, 362/96, 643, 642, 802; 392/386–393
See application file for complete search history.

(56) References Cited

U.S. PATENT DOCUMENTS 3,967,545 A   7/1976   Baker (Continued)

FOREIGN PATENT DOCUMENTS

EP   0882459   12/1998

(Continued)

OTHER PUBLICATIONS

Candle Breeze™, CandleBreeze® Makes Great Scents, Catalog Product Sheet, available at http://www.thecandlewarmer.com/index.cfm?fuseaction=Catalog.Candle%20Breeze™, Mar. 15, 2007.

(Continued)

*Primary Examiner*—Laura Tso
(74) *Attorney, Agent, or Firm*—Gordon & Jacobson, PC (57) ABSTRACT

A flameless candle includes a translucent housing having a concavity in its top resembling a partially melted pillar candle. A false wick is mounted in the center of the concavity. A circuit board containing an LED, an integrated circuit chip, and an ambient light sensor is mounted inside the housing below the false wick. A battery compartment and a fragrance cartridge compartment are located in the bottom of the housing together with a slide switch. The housing also includes an electric fan or blower mounted adjacent to the fragrance cartridge compartment. The slide switch selectively completes an electrical circuit between the batteries and the circuit board, the batteries and the fan, or both. The fan is arranged such that, when activated, it blows air into the cartridge compartment. The fragrance cartridge and the cartridge compartment are designed to allow the air to pass through the fragrance cartridge (where the air becomes scented by the fragrance) and pass upward to exit the housing through holes in the upper concavity of the housing. According to one aspect of the invention, the fragrance contained in the fragrance cartridge is an insect repelling fragrance such as geraniol, preferably mixed with other fragrances.

19 Claims, 5 Drawing Sheets

U.S. PATENT DOCUMENTS

| | | | |
|---|---|---|---|
| 4,301,783 | A | 11/1981 | Buckner et al. |
| 4,510,556 | A | 4/1985 | Johnson |
| 4,816,973 | A * | 3/1989 | Atalla et al. .............. 362/643 |
| 5,810,895 | A | 9/1998 | Staehle et al. |
| 6,413,476 | B1 | 7/2002 | Barnhart |
| 6,454,425 | B1 | 9/2002 | Lin |
| 6,966,665 | B2 | 11/2005 | Limburg et al. |
| 7,029,146 | B2 | 4/2006 | Kitchen |
| 7,132,084 | B1 | 11/2006 | Roumpos |
| 2002/0080601 | A1 | 6/2002 | Meltzer |
| 2003/0007887 | A1 | 1/2003 | Roumpos et al. |
| 2004/0257798 | A1 * | 12/2004 | Hart et al. .................. 362/96 |

FOREIGN PATENT DOCUMENTS

| | | |
|---|---|---|
| EP | 1283062 | 2/2003 |
| GB | 2285579 | 7/1995 |
| WO | WO 95/10352 | 4/1995 |
| WO | WO01/02025 | 1/2001 |
| WO | WO01/23008 | 4/2001 |
| WO | WO02/30220 | 4/2002 |
| WO | WO02/31413 | 4/2002 |
| WO | WO03/086487 | 10/2003 |
| WO | WO2005/003623 | 1/2005 |

OTHER PUBLICATIONS

Large Candle Breeze™, CandleBreeze® Makes Great Scents, Catalog Product Description, available at http://www.thecandlewarmer.com/index.cfm?fuseaction=Catalog. ViewProduct&productid=6, Mar. 15, 2007.

Fragrance Without a Flame™, CandleBreeze® Makes Great Scents, product description sheet, available at www.thecandlewarmer.com/, Mar. 15, 2007.

Company Description, CandleBreeze® Makes Great Scents, available at www.thecandlewarmer.com/index.cfm?fuseaction=Home.ViewPage&page_id=5451A4F0-D9A6-4A09-A6BBB7B2A76F8304, Mar. 15, 2007

Market and Operating Parameters for Pende Products, CandleBreeze® Makes Great Scents, available at www.thecandlewarmer.com/index.cfm?fuseaction=home. ViewPage&page_id=8C38D2E4-2078-03EB-5199796C71BB4E09, downloaded Mar. 15, 2007.

Products, CandleBreeze® Makes Great Scents, available at www.thecandlewarmer.com/index.cfm?fuseaction=Home. ViewPage&page_id338DE0FC-DA92-443B-B261B43BDC98E07D, downloaded Mar. 15, 2007.

Vanilla-Scented Battery-Operated Wax Candle Flickers Like It's Real, Catalog Description, Smarthome Electronic Home Improvement & Automation Superstore, available at www.smarthome.com/4611BD.html?src=HML07RA58, downloaded Apr. 24, 2007.

* cited by examiner

FLAMELESS CANDLE INCORPORATING INSECT REPELLANT DIFFUSER AND AN AMBIENT LIGHT SENSOR

CROSS-REFERENCE TO RELATED APPLICATIONS

This application claims benefits from U.S. Provisional Patent Application No. 60/834,597, filed Aug. 1, 2006, the contents of which are hereby incorporated herein by reference.

BACKGROUND OF THE INVENTION

1. Field of the Invention

This invention relates broadly to flameless candles. More particularly, this invention relates to a flameless candle which incorporates an insect repellant diffuser and an ambient light sensor.

2. State of the Art

The Egyptians were using wicked candles in 3,000 B.C., but the ancient Romans are generally credited with developing the wicked candle before that time by dipping rolled papyrus repeatedly in melted tallow or beeswax. The resulting candles were used to light their homes, to aid travelers at night, and in religious ceremonies.

Women in colonial America discovered that boiling the berries of bayberry bushes produced a sweet-smelling wax that burned cleanly. However, extracting the wax from the bayberries was extremely tedious. As a result, the popularity of bayberry candles soon diminished.

During the latter twentieth century, interest in candles increased, particularly in scented candles which are used to mask an unpleasant odor in a room or to create a mood.

Candles, however, can be dangerous. This is particularly so when candles are used around children or in a breezy environment where candles can become a serious fire hazard. Candles also have the disadvantage of often creating a mess of the melted wax which can stick to furniture, placemats, etc. and is difficult to remove. In addition, most candles do not last very long and may appear ugly after burning for some time.

With the dangers and disadvantages of candles in mind, electrically powered flameless candles were developed soon after the invention of the electric light bulb. With the development of the light emitting diode (LED), compact, low-powered, realistic flameless candles became available.

The typical flameless candle available today uses one or more LEDs powered by AA cells. A circuit is included which causes the LED(s) to flicker giving the appearance of a real flame. These candles are lacking, however, in that they do not completely simulate a real candle. Also, while the dangers associated with real candles provide an incentive to extinguish candles before leaving them unattended, this is not so with flameless candles. The safety of flameless candles provides no important incentive to turn them off before falling asleep, for example. When that happens, the flameless candle will "burn" throughout the night and following day. This will rapidly consume AA cells and lead to unnecessary expense.

U.S. Pat. No. 6,966,665 discloses a flameless candle with an air intake chamber and an air outflow chamber. A liquid fragrance container is provided with a wick in fluid communication with the liquid fragrance. A fan is located adjacent the wick. The fan draws air into the air intake chamber, past the fragrance wick and out the outflow chamber. This can give a simulation of a scented candle. However, if the candle tips over, the liquid can spill.

U.S. Patent Application Publication Number US 2003/0007887 discloses an aromatic substance heating device which in one embodiment includes a light source which simulates the appearance of a burning candle. This device also has the disadvantage that the heated aromatic substance is a liquid which, if the device tips over, can spill and cause a mess. In at least one embodiment, the aromatic substance is a solid that liquefies when heated, like wax, and when it spills it will solidify like wax causing a wax-like mess which is difficult to clean up. Furthermore, electrical devices which generate heat generally consume a lot of energy. Thus, it is likely that the batteries will not last long.

Finally, there is one disadvantage shared by both real candles and state of the art flameless candles. When many candles are spread throughout the house to celebrate a holiday, for example in windows during winter holidays, one must remember to light them at dusk and extinguish or turn them off before dawn.

SUMMARY OF THE INVENTION

It is therefore an object of the invention to provide a flameless candle.

It is another object of the invention to provide a flameless candle which accurately simulates more aspects of real candles than existing flameless candles do.

It is a further object of the invention to provide a flameless candle which automatically conserves power.

It is also an object of the invention to provide a flameless candle which is versatile and can be operated in several modes.

It is an additional object of the invention to provide a flameless candle which is quickly and easily adapted to different applications or uses.

It is still another object of the invention to provide a flameless candle which lights itself automatically.

In accord with these objects, which will be discussed in detail below, a flameless candle according to the invention includes a translucent housing having a concavity in its top resembling a partially melted pillar candle. A false wick is mounted in the center of the concavity. A circuit board on which are mounted an LED, an integrated circuit chip, and an ambient light sensor is located inside the housing below the false wick. A battery compartment and a fragrance cartridge compartment are located in the bottom of the housing together with a slide switch. The housing also includes an electric fan or blower mounted adjacent to a fragrance cartridge compartment. The slide switch selectively completes an electrical circuit between the batteries and the circuit board, the batteries and the fan, or both. The lower part of the housing is provided with small legs which lift it up from the surface upon which it is placed to accommodate the switch and to allow air to enter the housing from a vent in the bottom. The fan is arranged such that, when activated, it blows air from the vent in the bottom of the housing into the cartridge compartment. The fragrance cartridge and the cartridge compartment are designed to allow the air to pass through the fragrance cartridge (where the air becomes scented by the fragrance) and pass upward in the housing to exit the housing through a plurality of holes in the upper concavity of the housing.

According to one aspect of the invention, the fragrance contained in the fragrance cartridge comprises insect repelling fragrance infused polymer pellets.

According to another aspect of the invention, the slide switch is coupled to the components so that several different modes of operation are possible. These modes include fan only, LED only, fan and LED.

According to a further aspect of the invention, the ambient light sensor is connected to the circuit in a manner such that the LED will not operate in daylight or above a certain threshold of ambient room lighting.

In one mode of operation, the ambient light sensor will also automatically turn on the LED when ambient light conditions darken.

Another mode of operation is provided where the ambient light sensor is arranged to shut off the fan when the LED is shut off and to turn it on when the LED is turned on.

According to yet another aspect of the invention, access to the fragrance cartridge compartment is provided via a door in the bottom of the housing. This allows the user to change scents by changing the fragrance cartridge.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
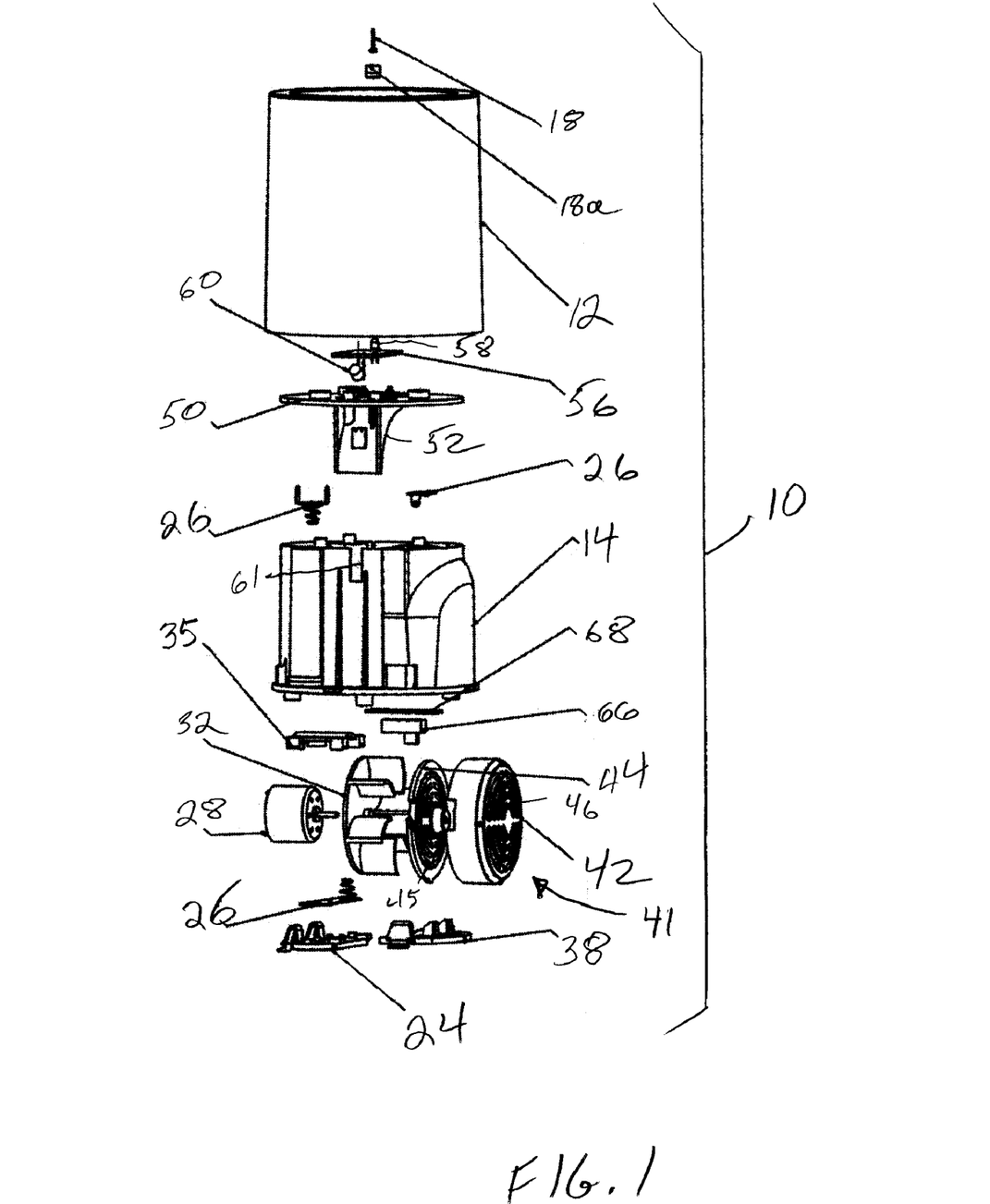
FIG. 1 is an exploded perspective view showing the components of a first embodiment of the invention.

Turning now to FIG. 1, a flameless candle 10 according to the invention includes a two-part housing which comprises an upper translucent part 12 and a lower opaque part 14. The upper translucent housing part 12 preferably formed from 1/10 inch thick polypropylene is hollow and generally cylindrical or slightly frustoconical with its uppermost diameter (e.g., 3.5 inches) being slightly less than its lowermost diameter (e.g., 3.75 inches), and a height of, e.g., 4 inches. The main features of the upper housing part 12 are best seen in FIGS. 3 and 5-7. They include a concave top surface 16 which is intended to give the appearance of a partially melted pillar candle. A false (e.g., black rubber) wick 18 is mounted (via mount 18a) in the center of the concave top surface 16 and the surface is provided with a plurality of vent slots 20. As illustrated, there are eight vent slots 20 arranged in a circle.

Figures 5, 6, 7:
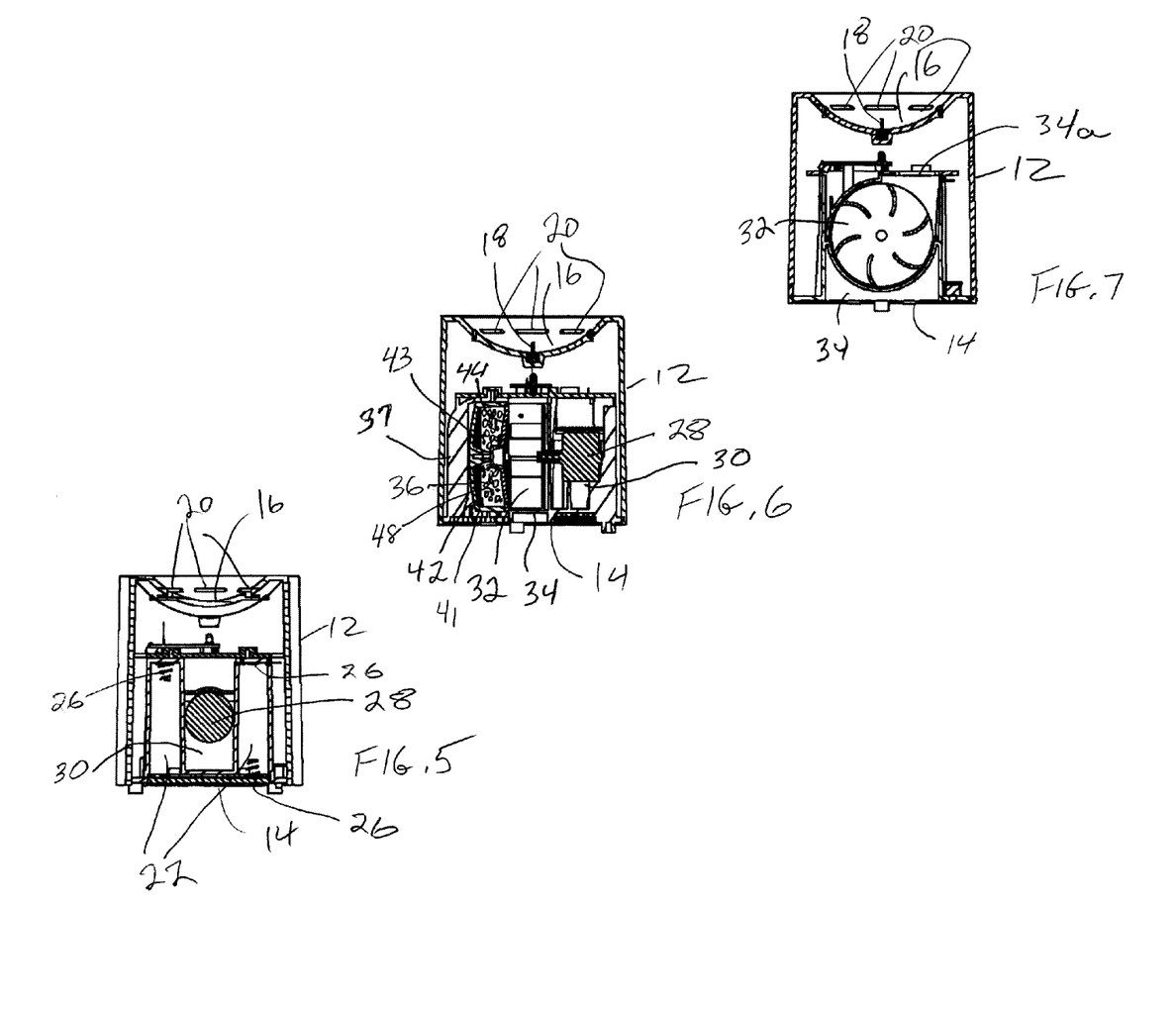
FIG. 5 is a sectional view taken along line A-A in FIG. 4.
FIG. 6 is a sectional view taken along line B-B in FIG. 4.
FIG. 7 is a sectional view taken along line C-C in FIG. 3.
Figure 8:
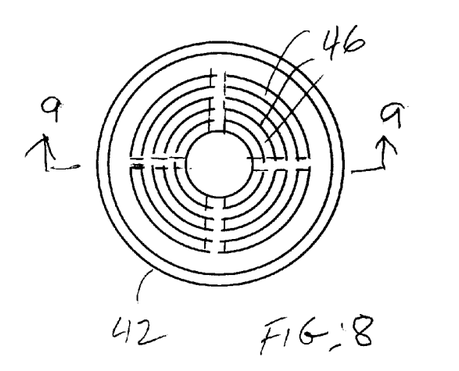
FIG. 8 is a top plan view of a fragrance cartridge according to a first embodiment of the invention.
Figure 9:
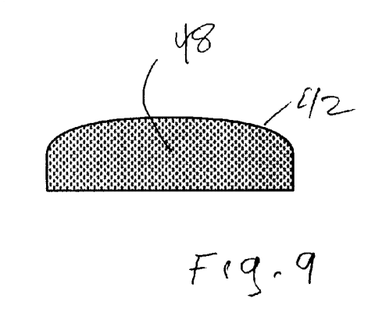
FIG. 9 is a sectional view taken along line 9-9 in FIG. 8.

The lower housing part 14 preferably formed from an opaque acrylonitride butadiene styrene (ABS) can be considered to have several compartments which house different parts of the apparatus. There is a battery compartment 22 which is actually two spaced apart compartments as shown in FIG. 5. These compartments 22 are designed to accommodate one AA cell each and are accessed via a single battery compartment door 24 on the bottom of the lower housing part 14. The battery compartments 22 and door 24 have associated electrical contacts and springs 26 which are conventional in the art of AA cell battery compartments.

As seen best in FIG. 5, an electric motor 28 is located in a compartment 30 which is in between the battery compartments 22. The motor 28 is coupled to a "squirrel cage" 32 which is located in a central compartment 34. Together, the motor 28 and squirrel cage 32 form a blower. The motor 28 is preferably provided with a cap 35 which acts to muffle motor noise.

Figure 4:
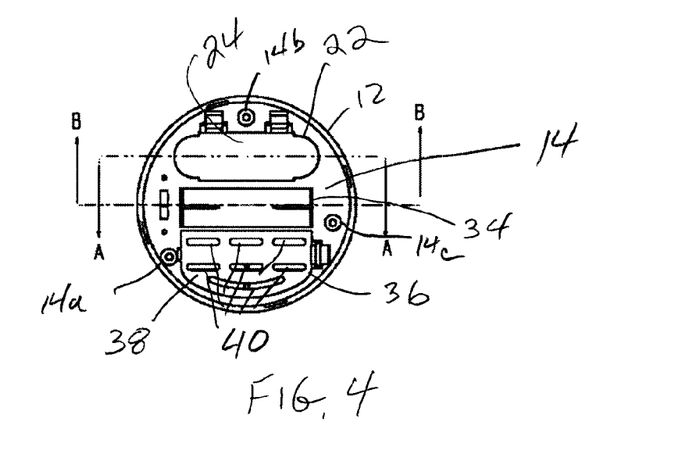
FIG. 4 is a bottom plan view of the exterior of the housing.

A fragrance cartridge compartment 36 is located adjacent to the central compartment 34 as seen best in FIG. 6. As seen in FIG. 4, the fragrance cartridge compartment 36 is closed by a door 38 with a plurality of vents 40 on the bottom of the lower housing part. The fragrance compartment 36 is open to the squirrel cage 32 and is provided with a thin vane 37, seen best in FIG. 6, which is perpendicular to the wall opposite the squirrel cage and serves to locate a fragrance cartridge 41 up against the squirrel cage compartment 34 and spaced from the outer wall of the housing 14.

According to this embodiment and as seen best in FIGS. 1, 6, 8, and 9, a puck-shaped fragrance cartridge 41 comprises a basket 42, fragrance-infused polyethylene pellets 48, and a cover 44. The basket 42 is provided with a plurality of vents 46 and the cover 44 is provided with a similar plurality of vents 45. The basket and cover are attached to each other by a central screw 43 with the polyethylene pellets 48 captured in the basket. The pellets are impregnated with a fragrance which is preferably an insect-repellent fragrance. According to a presently preferred embodiment, the pellets are mixed with fragrance according to the following proportions: 16% geraniol, 1% mint oil, 1% cinnamon oil, and 82% polyethylene. The pellets are available from Fasst Products, Brooklyn, N.Y. The technology of generating scented pellets is disclosed in U.S. Pat. Nos. 5,665,697 and 5,300,489 which are hereby incorporated by reference herein in their entirety. Other insect-repellent fragrances could also be utilized such as citronella.

Figure 2:
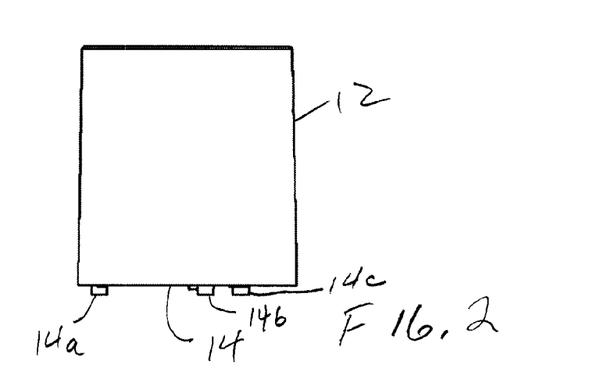
FIG. 2 is a side elevation view of the exterior of the housing.
Figure 3:
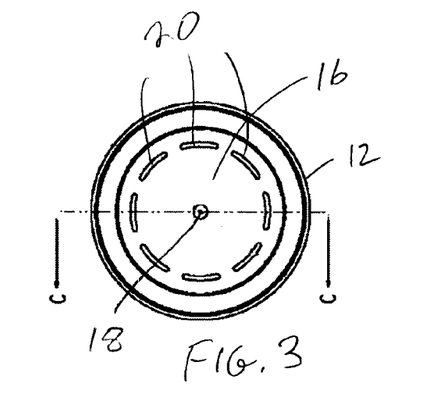
FIG. 3 is a top plan view of the exterior of the housing.

As seen best in FIGS. 2 and 4, the lower housing part 14 is provided with three legs 14a-14c which, among other things, provide an air space between the vented fragrance cartridge compartment door 38 and the surface upon which the candle is placed. As seen best in FIGS. 7 and 10, the top of the central compartment 34 containing the squirrel cage 32 has an air outlet 34a. From the foregoing, those skilled in the art will appreciate that when the motor 28 is activated, the squirrel cage 32 will spin. The vanes of the squirrel cage are arranged to cause air to be drawn through the vents 40 in the door 38, into the spaces between the housing wall and the cartridge 41, through the cartridge 41 (i.e., through the vents 46 in the front wall of the basket 42, the spaces between the pellets, and through the vents 45 in the basket cover 46), into the squirrel cage 32 and out from the air outlet 34a. From there, the air exits the upper housing part 12 through the slots 20 diffusing the scent from the fragrance cartridge compartment.

Figure 10:
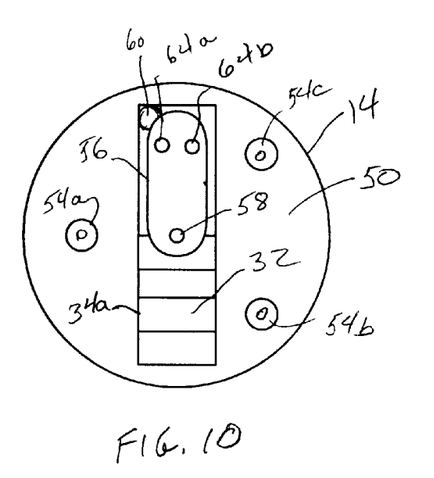
FIG. 10 is top plan view of the lower housing part.
Figure 11:
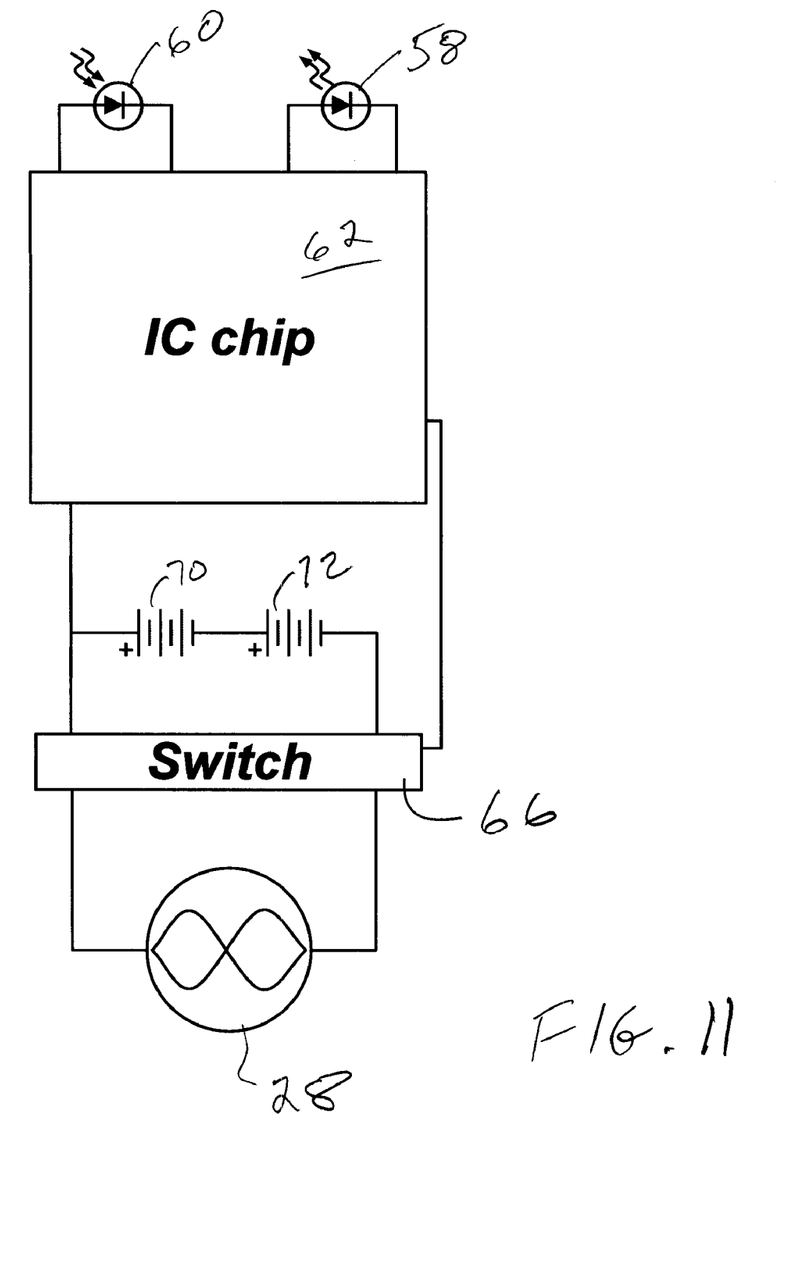
FIG. 11 is a high level schematic block diagram of the electrical components.

As seen best in FIGS. 1 and 10, the lower housing part 14 is further provided with an opaque cap or cover 50 which defines the aforementioned air outlet 34a and has a depending squirrel cage baffle 52. The cap 50 is secured to the housing 14 by three screws 54a-54c. The cap 50 also supports a circuit board 56 which supports an LED 58, a photocell 60, and an integrated circuit chip 62 (shown schematically in FIG. 11). The circuit board 56 is coupled to the cap 50 by screws 64a and 64b and is electrically coupled to a slide switch 66 (mounted on another circuit board 68) by wires (shown schematically in FIG. 11). The switch 66 is also electrically coupled by wires (shown schematically in FIG. 11) to the motor 26 and to batteries 70, 72 (FIG. 11) via the battery contacts 26 in the battery compartment 22. It is worth noting that the photocell 60 is located adjacent a peripheral wall of the housing 14 and to the underside of the circuit board 56 (which is rounded so as to only partially overlie the photocell), while the LED 58 is mounted on the upper side of the circuit board 56 in the middle of the flameless candle 10 under the wick. This arrangement in which the photocell 60 is partially shielded by the circuit board 56 and distant the LED 58 prevents "feedback" of light from the LED to the photocell which would cause the LED to flash on and off in the dark. In this embodiment, the lower housing part 14 is opaque and is therefore provided with a notch or "window" 61 adjacent to the photocell 60 so that light passing through the translucent upper housing part may reach the photocell through the lower housing part 14. In addition, by being opaque, the lower housing part 14 shields the motor and fan and shadows thereof from being seen through the translucent shell 12, and thereby permits the flameless candle in operation to appear very much like an actual candle.

The slide switch 66 selectively completes an electrical circuit between the batteries 70, 72 and the integrated circuit 62, the batteries and the fan motor 28, or both. According to one aspect of the invention, the slide switch is coupled to the components so that several different modes of operation are possible. These modes include fan-only, LED-only, and fan and LED. The photocell 60 is arranged to automatically control the LED when in LED only or fan and LED mode such that the LED is shut off when ambient light reaches a threshold of brightness and turned on when ambient light reaches a threshold of darkness. According to an alternate embodiment, a fourth mode of operation is provided where the photocell 60 is arranged to shut off the fan when the LED is shut off and to turn it on when the LED is turned on.

There have been described and illustrated herein embodiments of a flameless candle incorporating an insect repellent diffuser and an ambient light sensor. While particular embodiments of the invention have been described, it is not intended that the invention be limited thereto, as it is intended that the invention be as broad in scope as the art will allow and that the specification be read likewise. Thus, while a particularly preferred insect repellent mixture has been disclosed, it will be appreciated that other mixtures of other ingredients could be used. Also, while particular sizes have been described, it will be appreciated that the flameless candle may assume different sizes. It will therefore be appreciated by those skilled in the art that yet other modifications could be made to the provided invention without deviating from its spirit and scope as claimed.

What is claimed is:

1. A flameless candle, comprising:
   a translucent housing defining at least one vent hole;
   an LED mounted inside said translucent housing;
   a fan or blower mounted inside said housing;
   a scent cartridge mounted inside said housing and adjacent said fan or blower, said scent cartridge containing a plurality of plastic pellets impregnated with an insect repelling scent;
   a switch electrically coupled to said LED and said fan or blower; and
   a battery compartment mounted inside said housing and having electrical contacts electrically coupled to said switch, wherein
   said switch is operable to activate said LED and said fan when batteries are placed in said battery compartment, and said fan, when activated, causes air to move through said scent cartridge and out of said at least one vent hole.

2. A flameless candle according to claim 1, further comprising:
   an ambient light sensor electrically coupled to said LED such that said LED is activated only when ambient light is at or below a threshold darkness.

3. A flameless candle according to claim 1, further comprising:
   an inner housing over which said translucent housing extends, said inner housing defining a first compartment in which said fan or blower is located, a second compartment in which said scent cartridge is located, and said battery compartment, said scent cartridge being removable from said inner housing and replaceable.

4. A flameless candle according to claim 2, wherein:
   said ambient light sensor is electrically coupled to said fan or blower such that said fan or blower is activated only when said LED is activated.

5. A flameless candle according to claim 2, further comprising:
   a circuit board on which said LED is mounted on one side and said ambient light sensor is located on the opposite side.

6. A flameless candle according to claim 1, wherein:
   said switch is operable to activate said LED but not said fan or blower, to activate said fan or blower but not said LED, or to activate both said LED and said fan or blower.

7. A flameless candle according to claim 6, further comprising:
   an ambient light sensor electrically coupled to said switch, wherein said switch is operable to include said ambient light sensor in circuit with said LED, said fan or blower, or both.

8. A flameless candle according to claim 3, wherein:
   said scent cartridge comprises a basket and a plurality of said plastic pellets, said basket having vents on opposite sides and said basket containing said plastic pellets, and
   said inner housing includes means in said second compartment for locating said scent cartridge adjacent said first compartment and away from an outer wall of said inner housing.

9. A flameless candle, comprising:
   a translucent housing defining at least one vent hole;
   an LED mounted inside said translucent housing;
   a fan or blower mounted inside said housing;
   a scent-impregnated plastic adjacent said fan or blower;
   a switch mounted electrically coupled to said LED and said fan or blower;
   a battery compartment mounted inside said housing and having electrical contacts electrically coupled to said switch;
   an ambient light sensor electrically coupled to said LED, said ambient light sensor being arranged to prevent said LED from being activated when ambient light is at or above a threshold of brightness; and
   a circuit board to which said LED is mounted on one side and said ambient light sensor is located on the opposite side, wherein
   said switch is operable to activate said LED and said fan when batteries are placed in said battery compartment, and said fan, when activated, blows air at said scent-impregnated plastic and out of said at least one vent hole.

10. A flameless candle according to claim 9, wherein:
    said LED is mounted central in said flameless candle, and said ambient light sensor is located near a side wall of said translucent housing.

11. A flameless candle according to claim 9, further comprising:

an inner housing over which said translucent housing extends, said fan or blower, said scent cartridge, and said battery compartment being located inside said inner housing, wherein said scent cartridge contains insect repelling scented pellets, and said scent cartridge is removable from said inner housing and replaceable.

12. A flameless candle according to claim 9, wherein:
said switch is operable to activate said LED but not said fan or blower, to activate said fan or blower but not said LED, or to activate both said LED and said fan or blower.

13. A flameless candle according to claim 9, wherein:
said switch is operable to activate both said LED and said fan or blower with said ambient light sensor being arranged to deactivate said fan or blower when said LED is deactivated.

14. A flameless candle, comprising:
an outer translucent housing defining at least one vent hole;
an inner housing defining first, second, and third compartments and an outer wall;
an LED mounted outside said inner housing and inside said outer translucent housing;
a fan or blower mounted inside said first compartment;
a scent cartridge mounted inside said second compartment and adjacent said fan or blower wherein said inner housing includes means in said second compartment for locating said scent cartridge adjacent said first compartment and away from said outer wall of said inner housing;
a switch mounted on said inner housing and electrically coupled to said LED and said fan or blower;
said third compartment arranged for receiving at least one battery and having electrical contacts electrically coupled to said switch; wherein
when batteries are placed in said third compartment, said switch is operable to activate said LED but not said fan or blower, to activate said fan or blower but not said LED, or to activate both said LED and said fan or blower.

15. A flameless candle according to claim 14, further comprising:
an ambient light sensor electrically coupled to said LED such that said LED is activated only when ambient light is at or below a threshold darkness.

16. A flameless candle according to claim 15, wherein:
said ambient light sensor is selectively electrically coupled by said switch to said fan such that said fan turns on and off with said LED.

17. A flameless candle according to claim 15, further comprising:
a circuit board on which said LED is mounted on one side and central said flameless candle and said ambient light sensor is located on the opposite side and adjacent a side wall and a top wall of said inner housing.

18. A flameless candle according to claim 17, wherein:
said scent cartridge comprises a basket and a plurality of said plastic pellets, said basket having vents on opposite sides and said basket containing said plastic pellets.

19. A flameless candle according to claim 18, wherein:
said plastic pellets comprise insect-repellent fragrance infused plastic.

* * * * *